United States Patent [19]

Zoumalan

[11] Patent Number: 5,229,298
[45] Date of Patent: Jul. 20, 1993

[54] METHOD OF ANALYZING MARKER DYE CONCENTRATIONS IN LIQUIDS

[75] Inventor: Sarkiss Zoumalan, Moorpark, Calif.
[73] Assignee: Atlantic Richfield Company, Los Angeles, Calif.
[21] Appl. No.: 825,343
[22] Filed: Jan. 24, 1992
[51] Int. Cl.$^5$ .................. G01N 33/02; G01N 33/22
[52] U.S. Cl. ..................... 436/111; 436/106; 436/141; 436/139; 436/161; 73/23.38; 252/11
[58] Field of Search .......... 436/56, 106, 111, 139–142, 436/161; 73/23, 38, 61.1 C; 252/11

[56] References Cited

U.S. PATENT DOCUMENTS

| | | | |
|---|---|---|---|
| 4,049,393 | 8/1977 | Orelup | 44/59 |
| 4,209,302 | 6/1980 | Orelup | 44/59 |
| 4,764,290 | 8/1988 | Currey | 252/11 |
| 4,764,474 | 8/1988 | Orelup | 436/111 |
| 4,918,020 | 4/1990 | Nowak | 436/56 |

*Primary Examiner*—James C. Housel
*Assistant Examiner*—David Redding
*Attorney, Agent, or Firm*—Drude Faulconer

[57] ABSTRACT

A method for determining the concentration of a tracer, e.g. nitrogen-bearing marker dye, in a hydrocarbon liquid, e.g. gasoline. In the present method, a sample of the marked hydrocarbon liquid which is to be analyzied is prepared by adding a known volume of a nitrogen-bearing, "internal standard" thereto. The sample is then heated, preferably in a gas chromatograph, to vaporize, separate, and measure the dye and the internal standard. These measurements provide a ratio which is matched or compared to a predetermined, reference ratio which, in turn, is representative of a known concentration of the dye in the sampled hydrocarbon.

6 Claims, 2 Drawing Sheets

GAS CHROMATOGRAM OF DYE IN GASOLINE

GASOLINE PEAKS

GAS CHROMATOGRAM OF GASOLINE WITHOUT DYE

INTERNAL STANDARD PEAK (TRIOCTYLAMINE) $A_2$

TRACER DYE PEAK $A_1$

GASOLINE PEAKS

GAS CHROMATOGRAM OF DYE IN GASOLINE

METHOD OF ANALYZING MARKER DYE CONCENTRATIONS IN LIQUIDS

DESCRIPTION

Technical Field

The present invention relates to a method of analyzing marker dyes in liquids and in one aspect relates to a method for analyzing concentration of a nitrogen-bearing marker dye in a liquid hydrocarbon fuel to aid in identifying a particular, marked fuel.

Background Art

In marketing gasolines and other hydrocarbon fuels, refiners go to great expense to insure that their respective branded (trademarked) products will meet their respective, advertised and stringent specifications regarding volatility, octane number, etc. Further, the suppliers want to insure that those fuels which contain additives, e.g. detergents, or "clean" gasolines which contain substantial amounts of alcohols will be uniform and consistent when retailed. When a company maintains tight quality controls on its products, customers can rely upon that company's trademark to assure themselves that they are actually getting the quality of product that they are paying for.

Unfortunately, some dishonest fuel dealers have learned that they can make large profits by passing off inferior fuels as higher quality, branded products or by simply diluting the branded product with a cheaper, unmarked fuel. Although the trademarked companies are extremely sensitive to this problem, it is very difficult to ferret out those dealers who blend or dilute branded products with inferior products, especially gasolines. Since normally the blended products will continue to qualitatively display the presence of each component originally in the branded product, more expensive quantitative analysis is usually required to detect contamination or dilution of a branded product. Unfortunately, while the key ingredients of the branded product are still present in the blended fuel, they are in such low concentrations that any quantitative analysis is very difficult to administer, is very time consuming, and accordingly is relatively expensive.

A recognized technique for analyzing hydrocarbon fuels to aid in quality control involves adding a tracer or marker dye to the fuel before it is distributed to the dealers. One such well known marker dye is a nitrogen-bearing dye known as Marker MP Dye and is commercially available from Morton-Norwich Products, Inc., Chicago, Ill. This dye is routinely added to liquid hydrocarbon fuels such as gasoline as a tracer to aid in detecting possible trademark violations and such. When added in very low amounts it is non-visible and cannot be detected by other than chemical means. It can, however, be quantified by chemical analysis to determine the degree that a marked fuel has been adulterated with non-dyed products. To detect trademark violations, the dye manufacturer recommends a typical treat level of around 20 parts per million (ppm). Methodology and reagents for quantifying the dye at these treat levels are also available from the manufacturer. However, the costs of the dye and reagents for these treat levels are relatively expensive and may be prohibitive for many applications.

The methodology recommended by the dye manufacturer for quantification analysis of a gasoline marked with these dyes requires first extracting the dye from the gasoline with an acidic liquid extractant and then mixing the extracted dye with a color-forming reactant. The intensity of the resulting color is then measured after a timed interval in a colorimeter and is directly compared to a predetermined color which is representative of the actual concentration of dye in the analyzed gasoline. However, this procedure is (1) limited in sensitivity, (2) time dependent, (3) cumbersome to perform, (4) subject to variances and interferences due to a particular analyst's techniques, and (5) limited in sample throughput. Sample throughput is a critical parameter for large scale screening tests.

Recently, another method has been developed which uses marker dye for detecting the adulteration of a liquid hydrocarbon fuel wherein much lower concentrations of the marker dye (e.g. from about 0.2 to about 2 ppmv) can be used in originally marking the fuel; see U.S. Pat. No. 4,918,020, issued Apr. 20, 1990, and assigned to the present assignee. This method selectively extracts the dye from a sample of the fuel by passing the sample through a solid phase extraction column, e.g. silica, to separate the marker dye from the rest of the sample. The dye is then reacted with a color-forming reagent to form a colored complex, the intensity of which is then matched to a color representative of a known, previously determined concentration of the dye in the fuel. While this technique works well with standard, hydocarbon gasolines, it is severely and adversely affected by the presence of oxygenates (e.g. methy tertiary butyl ether, alcohols, etc.). Accordingly, its use is not recommended for analyzing gasolines containing such additives, e.g. "clean" gasolines which contain substantial volumes of alcohols such as methanol and/or ethanol.

SUMMARY OF THE INVENTION

The present invention provides a method for determining the concentration of a tracer, e.g. nitrogen-bearing marker dye, in a hydrocarbon liquid, e.g. gasoline. In the present method, a sample of the marked hydrocarbon liquid which is to be analyzed is prepared by adding a known volume of a nitrogen-bearing, "internal standard" thereto. The sample is then heated to vaporize and separate the dye and the internal standard so that they may be individually measured. The two measurements provide a ratio which, in turn, is matched to a predetermined, reference ratio which is representative of a known concentration of the dye in the sampled hydrocarbon liquid.

The preferred nitrogen-bearing marker dye is selected from the group consisting of 1-(4-morpholino)-3-(alpha naphthylamino)-propane and 1-(4-morpholino)-3-(beta naphthylamino)-propane of which only small amounts, e.g. from about 0.2 to about 5 ppm, are needed to mark the hydrocarbon. The "internal standard" is comprised of a nitrogen-bearing liquid, preferably trioctylamine, which is stable when mixed with the marked liquid hydrocarbon and which has a boiling point which is distinct from both the boiling points of the marker dye and the various hydrocarbon components in the marked liquid. This allows all of the various components in the analyzed liquid to be readily identified from each other as the sample is heated above the respective boiling points of the individual components.

The present method is preferably carried out in a commerically-available gas chromatograph (GC) having a capillary GC column which, in turn, has a cool "on-column" injector at its inlet and a nitrogen-phosphorus detector (NPD) at its outlet. The on-column injector system provides for sample injection at room temperature. An integrator is used to acquire and process the data. The marker dye separation is not affected by the presence of oxygenates.

The present method is sensitive to the nitrogen compound in the marker dye and has the capability of separating nitrogen compounds with boiling points below 243° C. in about 20 minutes without requiring any extensive sample preparation such as extraction or evaporation. The only sample preparation required in the present invention is the addition of the nitrogen-bearing internal standard to the sample before it is passed through the GC.

In carrying out the present invention, a series of individual, predetermined reference "ratios" are first compiled against which a later determined ratio can be matched or compared to thereby determine the concentration of a marker dye in an analyzed hydrocarbon liquid. These ratios are determined by adding an equal volume of internal standard, e.g. trioctylamine solution to several individual standard samples of the hydrocarbon liquid of interest, each sample having a different known concentration of a nitrogen-bearing dye. Each standard sample is then individually passed through a GC such as described above. As the sample passes through the capillary column of the GC, the hydrocarbon components in the sample elute first as they reach their respective boiling points. The internal standard (trioctylamine) elutes next and the marker dye shortly thereafter. The peak areas of both the dye and the internal standard are detected by the NPD on the GC column.

The ratio of the respective peaks areas of a particular standard sample is plotted against the known concentration of the marker dye in that respective sample. A regression analysis of the experimental data provides a linear relationship with a 0.9997 correlation coefficient. Once these reference ratios are compiled, a sample of a liquid to be analyzed is prepared in the same manner as were the standard samples and it is passed through the GC to obtain a marker dye/internal standard ratio in the same way as before. This ratio is then matched or compared to a particular predetermined, reference ratio which is representative of the concentration of the marker dye in the analyzed liquid. This concentration of marker dye can then be used to determine whether or not a particular marked fuel has been tampered with or it can be used to identify a particular grade of gasoline, etc., depending on the set of reference ratios used.

Gas chromatographic analysis of thermally labile nitrogen compounds such as the present marker dyes is not free of trouble. For example, the attachments such as the on-column, the NPD detector, the long needle syringe, etc. may introduce errors and uncertainities into the measurements of the nitrogen-bearing dye. The present invention alleviates these errors by adding an equal volume of a known nitrogen-bearing internal standard to each sample and using the ratio between the nitrogen-bearing marker dye to the internal standard as the determining measurement. That is, any errors present in the measurement of the dye will also be present in the measurement of the internal standard and will cancel each other when the ratio is taken.

BRIEF DESCRIPTION OF THE DRAWINGS

The actual operation and apparent advantages of the present invention will be better understood by referring to the drawings in which.

BEST KNOWN MODE FOR CARRYING OUT THE INVENTION

Figure 1:
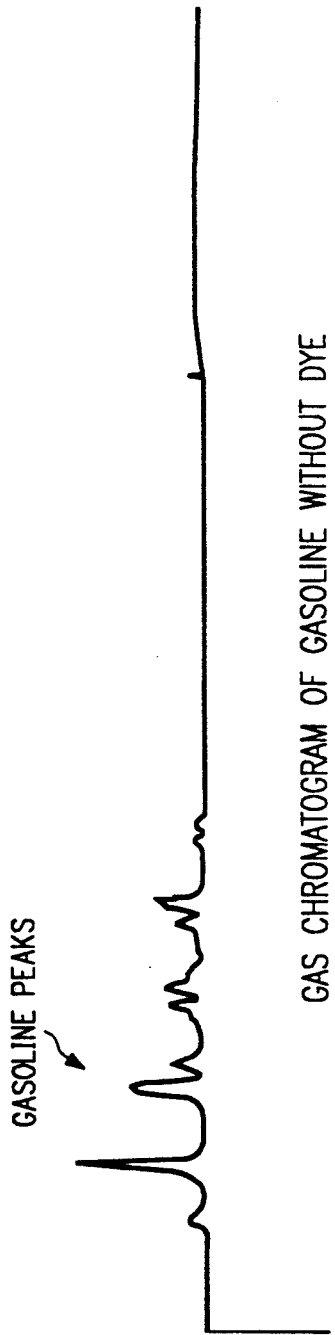
FIG. 1 is a typical chromatogram of a hydrocarbon liquid fuel, i.e. gasoline having no additives therein.

The present invention provides a method for analyzing a nitrogen-bearing marker dye in a liquid hydrocarbon liquid, e.g. gasoline, which is useful in (1) determining if a marked hydrocarbon liquid has been contaminated with an unmarked or inferior liquid; (2) determining the amount of a particular additive in a hydrocarbon fuel, e.g. amount of alcohol in "clean" gasolines; and (3) other similar applications as they become apparent. In the present method, a sample of the marked hydrocarbon liquid to be analyzed is prepared by simply adding a known volume of a nitrogen-bearing, reference liquid (referred to herein as "internal standard") to the sample. The sample is then heated to vaporize and separate the dye and the internal standard so that they may be individually measured. The two measurements provide a ratio which, in turn, is matched or compared to a predetermined ratio which, in turn, is representative of a known concentration of the dye in the sampled hydrocarbon liquid.

More specifically, U.S. Pat. No. 4,209,302, issued Jun. 24, 1980 to Orelup (the disclosure of which is incorporated herein by reference) discloses nitrogen-bearing dyes which can be used in carrying out the present invention. Generally, these dyes comprise 1-(amino)-3-(alpha or beta naphthylamino)-propanes. The amine at the one position can be a secondary or tertiary amine and may be part of a ring structure. The preferred marker dye used in the invention is selected from the group consisting of 1-(4-morpholino)-3-(alpha naphthylamino)-propane and 1-(4-morpholino)-3-(beta naphthylamino)-propane. In many previous applications, this type of dye is recommended to be added to fuels and the like in relative large amounts, e.g. around 20 ppmv, thereby making their use expensive and sometimes prohibitive. The present invention allows these dyes to be added in substantially lesser amounts, e.g. from about 0.2 to about 5 ppm, which substantially reduces the costs involved in marking and monitoring the fuels. Such dyes are commercially available from Morton-Norwich Products, Inc.; Chicago, Ill.

The internal standard used in the present invention is a nitrogen-bearing liquid which is stable when mixed with the marked liquid hydrocarbon and one which has a boiling point that is distinct from both the boiling point of the marker dye and the boiling points of the various hydrocarbon components in the marked liquid. This is necessary so that both the vaporized dye and the internal standard can be readily identified from each other and from the vaporized hydrocarbon components when the sample is heated above the respective boiling points of its components. In developing the present invention, the following nitrogen-bearing compounds were either tested or evaluated with the following results:

| COMPOUND | BOILING POINT (°F.) |
|---|---|
| Methyl-3-Pyrrolidinol | 52 |
| Methylpyrrolidine | 81 |
| Pyrrolidine | 88 |
| Methy pyrrole | 112 |
| Pyridine | 114 |
| Pyrrolidinebutyronitril | 115 |
| Pyrrole | 131 |
| Octylamine | 177 |
| 2-Pyrrolidinemethanol | 187 |
| Aniline | 184 |
| N-Methylaniline | 196 |
| 2,3,3-Trimethylindolenine | 229 |
| Trioctylamine (TOA) | 367 |

Of the above, only trioctylamine ($[CH_3(CH_2)_7]_3N$) was found to the much preferred, if not the only, standard for use with the nitrogen-bearing marker dyes described above due to its stability and its boiling point of approximately 367° F. which lies between the substantially lower boiling points of the hydrocarbon components of the analyzed liquid and the boiling point (approximately 460° F.) of the preferred marker dyes. Once the internal standard liquid is added to the sample of the marked hydrocarbon liquid, the sample is heated to a temperature above the boiling point of the nitrogen-bearing marker dye ( i.e. highest boiling point of the components of interest) to vaporize the various components of the sample. This step is preferably carried out in a commerically available gas chromatograph (GC) such as described below.

A preferred gas chromatograph (e.g. Hewlett-Packard Model 5880) useful in carrying out the present invention has a 15 meter long capillary GC column, e.g. Model DB1, available from J & W Scientific, Folsom, Calif., with a 1 meter guard column installed thereon. The GC column has a cool "on-column" injector (see U.S. Pat. No. 4,440,550, available from J & W Scientific) at its inlet and a nitrogen-phosphorus detector (NPD), e.g. Part No. 19304, Hewlett-Packard Co., San Fernando, Calif., at its outlet. The on-column injector system provides for the sample to be injected at room temperature by elevating the injector assembly away from the heated zone of the GC until after the sample has been placed therein. The sample is placed in the on-column injector by a fused silica needle which has an inert metal oxide coating which, in turn, allows the needle to be inserted into a 0.25 mm I.D. inlet of the on-column injector on GC capillary columns as small as 0.25 mm I.D.. The length of the needle is 180 mm, 0.1 mm O.D., and may be attached to a 10-micro liter, gas-tight syringe. An intergrator (e.g. Hewlett-Packer Level Four Model) is used to acquire and process the data. The gas flow rates for the GC are set at: 100 ml/min for air; 4 ml/min for hydrogen; 30 ml/min for the carrier gas, helium. Continous flow rate of the carrier gas (helium free of oxygen) was monitored with a digital flow meter.

In carrying out the present invention, series of set of reference "ratios" must first be predetermined against which later actually measured ratios can be matched or compared to determine the concentration of a marker dye in hydrocarbon liquid (i.e. fuel) being analyzed. An example of a technique which can be used to arrive at a particular set of predetermined, reference ratios is as follows:

First, a 1% by volume (i.e. 10000 parts per million by volume (ppmv)) of trioctylamine, i.e. internal standard, is prepared in a 100 ml volumetric flask. To prepare this solution, 1.0 ml of trioctylamine is transferred into a 100 ml volumetric flask which is then filled with iso-octane. Then 10.0 ml of this stock solution is transferred to another 100 ml volumetric flask which is also filled to the mark with iso-octane. The latter solution now contains 1000 ppmv of trioctylamine which is then used to spike the fuel standards to be used to formulate the set of reference ratios.

Individual samples of a particular fuel of interest are prepared so each has a different known concentrations of a nitrogen-bearing dye (e.g. from about 0.5 to 5 ppmv). This may be done by transferring a measured amount of tracer dye from a 100 ppmv tracer stock solution into a 100 ml volumetric flask which is already filled to half volume with an unmarked fuel of interest. 2 ml of the 1000 ppmv of the previously prepared trioctylamine solution is transferred to each of these fuel samples and the respective flasks are filled to volume with additional unmarked fuel of interest. As seen from above, each sample is now spiked with the same amount of the internal standard (trioctylamine) but that the amount of dye in each is different.

After each of the reference samples have been prepared, each sample is passed through a GC such as described above. Using a a 10 microliter syringe having a fused silica needle 18 cm in length, approximately 2 microliters of a particular reference sample having a known concentration of marker dye is withdrawn from its respective flask and is directly injected into the on-column injector on the GC. At this point, the injector is fixed in an upright position above the inlet of the GC capillary column and is not lowered until the sample is in place within the injector.

The temperature at the injector port is maintained at 150° C. (302° F.) while the temperature of the oven is raised from 150° C. (302° F.) to 300° C. (572° F.) at a rate of about 15° C. (60° F.) per minute. The temperature of the nitrogen-phosphorus detector (NPD) at the outlet of the GC column is set slightly higher, e.g. 320° C. (608° F.), than the oven temperature in order to eliminate possible condensation which might otherwise form on the NPD detector. The collector current during the analysis is kept between 140 and 175, a dimensionless unit, which provides sufficient sensitivity and reproducible signals for both the internal standard and the marker dye.

Figure 2:
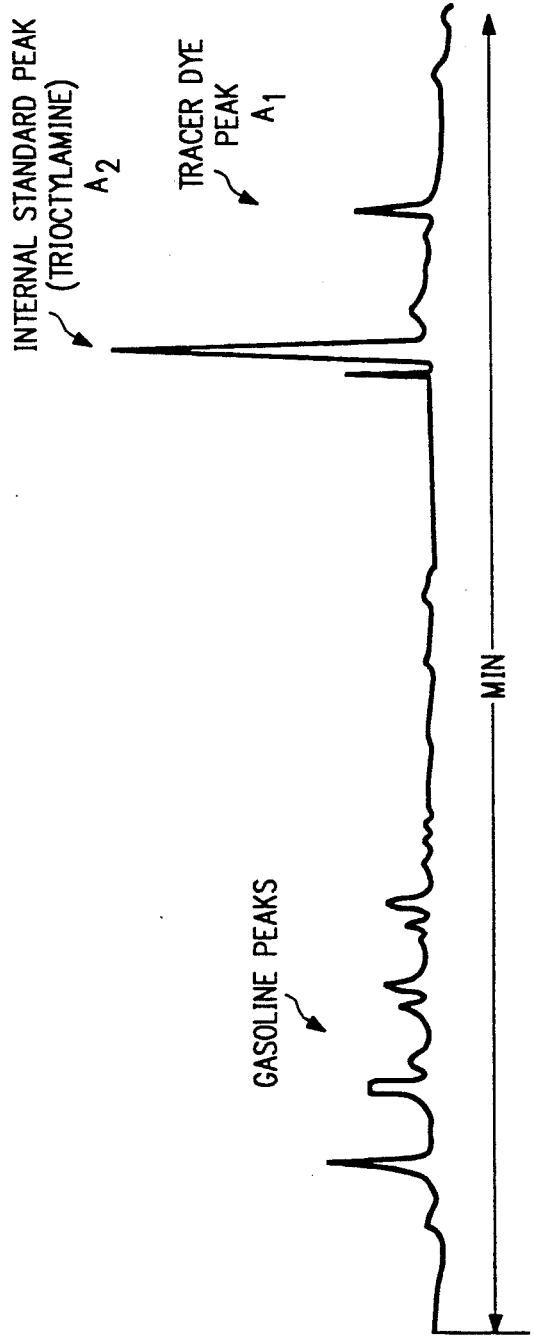
FIG. 2 is a typical chromatogram of the hydrocarbon liquid fuel of FIG. 1 with both a nitrogen-bearing internal standard and a nitrogen-bearing dye therein.

As a sample passes through the GC column, all of the hydrocarbon factions or components in the sample elute as they reach their respective boiling points which, in the present example, occurs within the first 8 minutes; see FIG. 1 which is a typical chromatogram of an unmarked hydrocarbon liquid (e.g. gasoline which contains no marker dye). The internal standard (trioctylamine) is eluted next at 13.35 minutes and the marker dye is last at 15.25 minutes; see FIG. 2 which is a typical chromatogram of a gasoline with both a nitrogen-bearing marker dye (area A1) and a nitrogen-bearing internal standard (area A2).

In the present example, reference ratios were predetermined for gasoline standards (prepared as described) above which contained 0.53, 1.07, 2.67, and 5.37 ppmv marker dye, respectively. These standard samples were analyzed as described above with the resulting data shown in Table 1 below.

TABLE 1

Marker Concentration vs. Reference Ratio Data

| Marker Concentration ppmv | Marker Area(A1) | Internal Standard(TOA) Area(A2) | Ratio A1/A2 |
|---|---|---|---|
| 0.53 | 14.79 | 110.58 | 0.133 |
| 0.53 | 24.58 | 193.21 | 0.127 |
| 0.53 | 26.88 | 194.80 | 0.137 |
| 0.53 | 42.73 | 324.32 | 0.132 |
| 0.53 | 18.07 | 131.67 | 0.137 |
| 0.53 | 13.22 | 107.07 | 0.123 |
| 1.07 | 48.89 | 185.47 | 0.263 |
| 1.07 | 43.93 | 161.40 | 0.272 |
| 1.07 | 55.41 | 199.23 | 0.278 |
| 1.07 | 26.23 | 103.82 | 0.252 |
| 1.07 | 30.58 | 108.93 | 0.280 |
| 1.07 | 32.37 | 118.00 | 0.274 |
| 2.67 | 125.43 | 156.97 | 0.799 |
| 2.67 | 89.63 | 118.83 | 0.754 |
| 2.67 | 109.25 | 145.25 | 0.752 |
| 2.67 | 122.55 | 160.85 | 0.761 |
| 2.67 | 90.72 | 114.31 | 0.793 |
| 2.67 | 46.36 | 65.69 | 0.705 |
| 5.37 | 247.66 | 159.44 | 1.553 |
| 5.37 | 219.67 | 138.33 | 1.588 |
| 5.37 | 229.22 | 148.32 | 1.545 |
| 5.37 | 171.20 | 107.80 | 1.588 |
| 5.37 | 122.34 | 77.59 | 1.576 |
| 5.37 | 173.80 | 113.78 | 1.527 |

Figure 3:
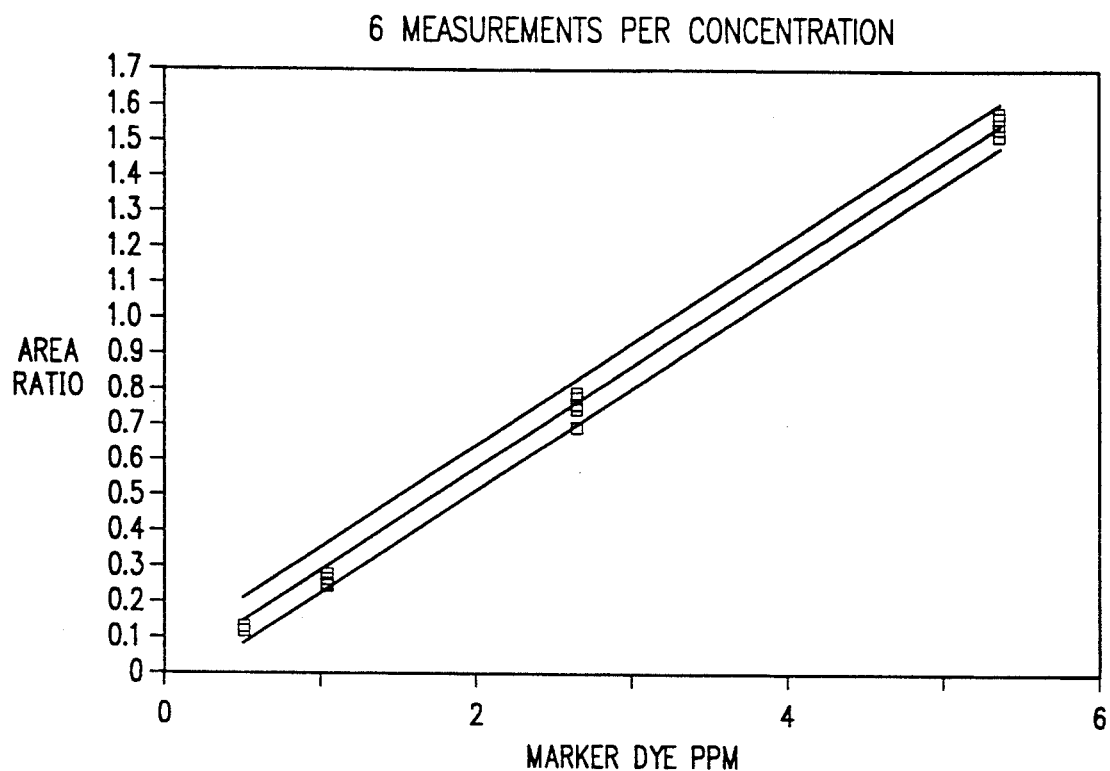
FIG. 3 is a graph plotting the area ratios (A1/A2 of FIG. 2) vs. the concentration of the nitrogen-bearing dye in the hydrocarbon liquid of FIG. 2.

The ratios of the peaks, i.e. the peak area of marker dye A1 divided by the peak area for the internal standard A2, were plotted against the concentrations of the marker dye in the respective samples, see FIG. 3. A regression analysis of the experimental data shown in Table 1 revealed a linear relationship with a 0.9997 correlation coefficient. This linear fit simplifies the calculation of the concentration of an unknown by using $Y = ax + b$ equation.

Once the above set of reference ratios for a hydrocarbon liquid, e.g. gasoline, have been predetermined, a sample of a hydrocarbon having an unknown marker dye concentration can then be prepared in the same manner as were the standard samples described above. The sample to be analyzed by the GC in the same way as described above to thereby establish a ratio between the internal standard and the marker dye in the sample. This ratio is now matched or compared to the predetermined ratios (FIG. 3 for the above example) to determine the actual concentration of the marker dye in the analyzed fuel. If the gasoline being analyzed is alleged to be a particular brand or grade of gasoline, then the concentration of the marker dye should be approximately the same as that which was originally present in the gasoline. If the measured dye concentration is less than the original concentraton, there is evidence that the fuel has been tampered with.

The present invention also has other benefits such as quantifying indirectly the amount of a known additive in a particular hydrocarbon liquid; e.g. amount of additive in a "clean" gasoline, thereby identifying a particular brand or grade of product. The use of the present invention to identify a particular product is similar to that described above in that a set of reference ratios are predetermined which are representative of respective, known concentrations of additives in a uniformly marked fuel. Again, the standard samples of the particular marked fuel are prepared in the same manner as described above and the standard samples are individual samples are passed through the GC to establish the respective ratios between the internal standard and the marker dye in each sample. For example, Table 2 below set forth the results of an actual analysis of a set of standard samples of a "clean" gasoline having varying concentrations of a known additive:

TABLE 2

Gasoline Additive Analysis Indirect Analysis

| Additive content VOL % | Dye content ppm | Ratio A1/A2 |
|---|---|---|
| 0.02 | 0.53 | 0.133 |
| 0.02 | 0.53 | 0.127 |
| 0.02 | 0.53 | 0.137 |
| 0.02 | 0.53 | 0.132 |
| 0.02 | 0.53 | 0.137 |
| 0.02 | 0.53 | 0.123 |
| 0.04 | 1.07 | 0.263 |
| 0.04 | 1.07 | 0.272 |
| 0.04 | 1.07 | 0.278 |
| 0.04 | 1.07 | 0.252 |
| 0.04 | 1.07 | 0.280 |
| 0.04 | 1.07 | 0.274 |
| 0.10 | 2.67 | 0.799 |
| 0.10 | 2.67 | 0.754 |
| 0.10 | 2.67 | 0.752 |
| 0.10 | 2.67 | 0.761 |
| 0.10 | 2.67 | 0.793 |
| 0.10 | 2.67 | 0.705 |
| 0.20 | 5.37 | 1.553 |
| 0.20 | 5.37 | 1.588 |
| 0.20 | 5.37 | 1.545 |
| 0.20 | 5.37 | 1.588 |
| 0.20 | 5.37 | 1.576 |
| 0.20 | 5.37 | 1.527 |

Figure 4:
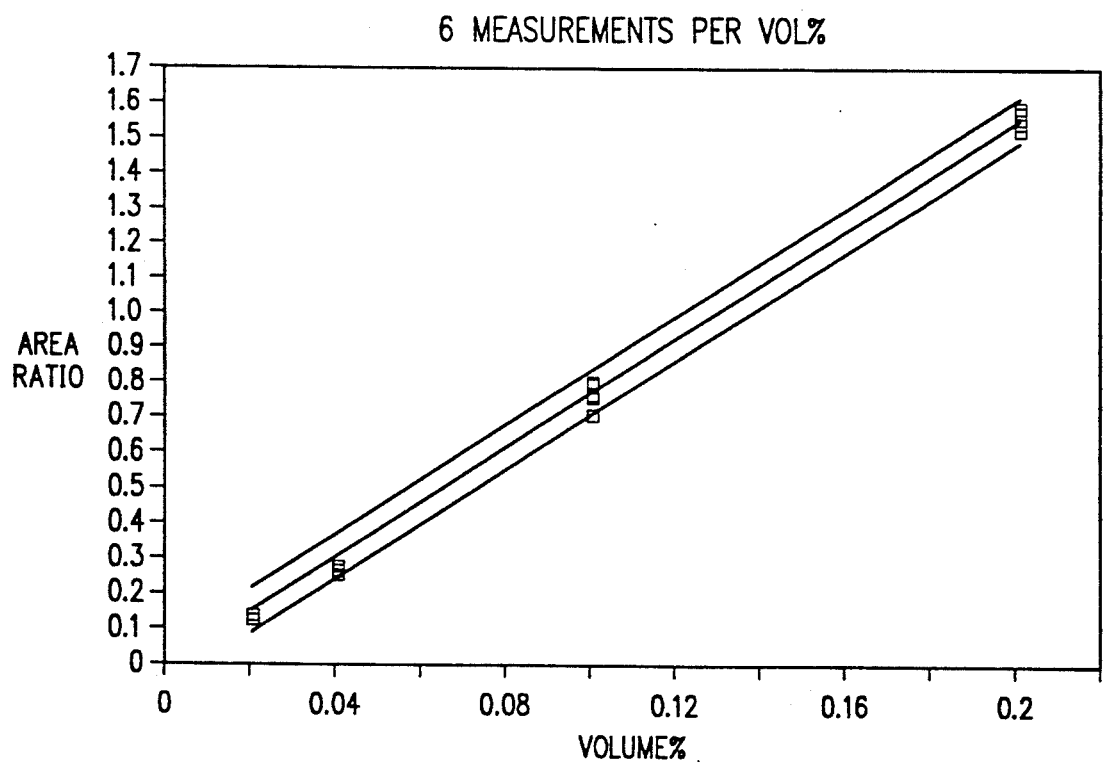
FIG. 4 is a graph plotting the area ratios (A1/A2 of FIG. 2) vs. the known concenrations of an additive in a hydrocarbon fuel.

Regression analysis of the concentrations of the additive vs. the ratios (A1/A2) also fit a linear equation with an approximate of 0.9997 correlation coefficient; see FIG. 4. Again, it can be seen that by comparing the internal standard/dye ratio in the analyzed fuel to a predetermined, reference ratios for known concentrations of additivies, the analyzed fuel can be readily identified.

What is claimed is:
1. A method for determining the concentration of a nitrogen-bearing marker dye is a liquid hydrocarbon wherein the nitrogen-bearing marker dye is selected from the group consisting of 1-(4-morpholino)-3-(alpha naphthylamino)-propane and 1-(4-morpholino)-3-(beta naphthylamino) propane, said method comprising;
   adding an internal standard to the liquid hydrocarbon containing the nitrogen bearing marker dye, said internal standard comprising a nitrogen-bearing liquid which is stable in said liquid hydrocarbon and which has a boiling point temperature different from that of said nitrogen-bearing marker dye;
   heating said liquid hydrocarbon containing said nitrogen-bearing marker dye and said nitrogen-bearing liquid internal standard to a temperature above higher of the boiling points of both said dye and said internal standard to thereby individually separate said dye and said internal standard;
   measuring both said separated nitrogen-bearing dye and said nitrogen-bearing internal standard and establishing a ratio between the two measurements, wherein the steps of heating said liquid hydrocarbon and the measuring said dye and said internal standard are carried out by passing said liquid hydrocarbon through a gas chromatograph, and determining the concentration of said dye by comparing said ratio with a predetermined reference ratio which is representative of the concentration of the marker dye in the hydrocarbon liquid.

2. The method of claim 1 wherein the nitrogen-bearing internal standard is trioctylamine.

3. A method for determining the concentration of a nitrogen-bearing marker dye in a liquid hydrocarbon wherein the nitrogen-bearing marker dye is selected from the group consisting of (1-(4-morpholino)-3-(alpha naphthylamino)-propane and 1-(4-morpholino)-3-(beta naphthylamino) propane, said method comprising:

taking a sample of said liquid hydrocarbon, adding an internal standard to said sample, said internal standard comprising a nitrogen-bearing liquid which is stable in said liquid hydrocarbon and having a boiling point temperature different from that of said nitrogen-bearing marker dye;

passing said sample through a capillary gas chromatograph column of a gas chromatograph while heating said sample to a temperature above the boiling points of both said dye and said internal standard to thereby individually separate said dye and said internal standard;

measuring both said separated nitrogen-bearing dye and said nitrogen-bearing internal standard and establishing a ratio between the two measurements; and determining the concentration of said dye by comparing said ratio with a predetermined reference ratio which is representative of the concentration of the marker dye in the hydrocarbon liquid.

4. The method of claim 3 wherein the nitrogen-bearing internal standard is trioctylamine.

5. The method of claim 4 wherein the nitrogen-bearing marker dye and said nitrogen-bearing internal standard are measured by a nitrogen-phosphorus detector positioned at the outlet of the capillary column of the gas chromatograph.

6. The method of claim 4 wherein the concentration of said nitrogen-bearing marker dye in said liquid hydrocarbon is from about 0.25 to about 5.0 ppms.

* * * * *